United States Patent
Mohr et al.

(10) Patent No.: US 9,597,153 B2
(45) Date of Patent: Mar. 21, 2017

(54) POSITIONS FOR MULTIPLE SURGICAL MOUNTING PLATFORM ROTATION CLUTCH BUTTONS

(71) Applicant: Intuitive Surgical Operations, Inc., Sunnyvale, CA (US)

(72) Inventors: Paul Mohr, Mountain View, CA (US); Michael Hanuschik, Mountain View, CA (US); Paul Millman, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 165 days.

(21) Appl. No.: 14/660,321

(22) Filed: Mar. 17, 2015

(65) Prior Publication Data
US 2015/0257840 A1   Sep. 17, 2015

Related U.S. Application Data (60) Provisional application No. 61/954,298, filed on Mar. 17, 2014.

(51) Int. Cl.
A61B 19/00   (2006.01)

(52) U.S. Cl.
CPC .......... *A61B 19/2203* (2013.01); *A61B 34/30* (2016.02); *A61B 34/35* (2016.02);
(Continued)

(58) Field of Classification Search
CPC .......... A61B 19/2203; A61B 2090/035; A61B 2090/508; A61B 34/30; A61B 34/35; A61B 34/37
See application file for complete search history.

(56) References Cited

U.S. PATENT DOCUMENTS

| 6,246,200 B1 | 6/2001 | Blumenkranz et al. |
| 6,459,926 B1 | 10/2002 | Nowlin et al. |

(Continued)

FOREIGN PATENT DOCUMENTS

| EP | 1885273 B1 | 2/2012 |
| WO | WO-0007503 A1 | 2/2000 |

(Continued)

OTHER PUBLICATIONS

Extended European Search Report for Application No. EP13829146.3, mailed on Mar. 15, 2016, 9 pages.
(Continued)

*Primary Examiner* — George Manuel (57) ABSTRACT

Robotic and/or surgical devices, systems, and methods include kinematic linkage structures and associated control systems configured to facilitate preparation of the system for use. One or more kinematic linkage sub-systems may include joints that are actively driven, passive, or a mix of both. A set-up mode employs an intuitive user interface in which one or more joints are initially held static by a brake or joint drive system. The user may articulate the joint(s) by manually pushing against the linkage with a force, torque, or the like that exceeds a manual articulation threshold. Articulation of the moving joints is facilitated by modifying the signals transmitted to the brake or drive system. The system may sense completion of the reconfiguration from a velocity of the joint(s) falling below a threshold, optionally for a desired dwell time. The system may provide a detent-like manual articulation that is not limited to mechanically pre-defined detent joint configurations. Embodiments of the invention provide, and can be particularly well-suited for manual movement of a platform supporting a plurality of surgical manipulators in a robotic surgical system or the like without having to add additional input devices.

15 Claims, 10 Drawing Sheets

(52) U.S. Cl.
CPC ........ *A61B 34/37* (2016.02); *A61B 2090/035* (2016.02); *A61B 2090/508* (2016.02)

(56) References Cited

U.S. PATENT DOCUMENTS

| | | | |
|---|---|---|---|
| 6,684,129 B2 | 1/2004 | Salisbury et al. | |
| 6,699,177 B1 | 3/2004 | Wang et al. | |
| 6,837,883 B2 | 1/2005 | Moll et al. | |
| 7,087,049 B2 | 8/2006 | Nowlin et al. | |
| 7,204,844 B2 * | 4/2007 | Jensen | A61B 34/76 606/205 |
| 8,004,229 B2 | 8/2011 | Nowlin et al. | |
| 2003/0013949 A1 | 1/2003 | Moll et al. | |
| 2004/0193146 A1 | 9/2004 | Lee et al. | |
| 2007/0142823 A1 | 6/2007 | Prisco et al. | |
| 2010/0161129 A1 | 6/2010 | Costa et al. | |
| 2010/0234857 A1 | 9/2010 | Itkowitz et al. | |
| 2011/0264108 A1 | 10/2011 | Nowlin et al. | |
| 2014/0052153 A1 | 2/2014 | Griffiths et al. | |
| 2014/0052154 A1 | 2/2014 | Griffiths et al. | |
| 2014/0276954 A1 | 9/2014 | Hourtash | |
| 2016/0081753 A1 | 3/2016 | Kostrzewski | |
| 2016/0081754 A1 | 3/2016 | Kostrzewski | |

FOREIGN PATENT DOCUMENTS

| | | |
|---|---|---|
| WO | WO-2006124390 A2 | 11/2006 |
| WO | WO-2007096322 A2 | 8/2007 |
| WO | WO-2011109041 A1 | 9/2011 |

OTHER PUBLICATIONS

International Search Report and Written Opinion for Application No. PCT/US13/55081, mailed on Dec. 2, 2013, 11 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

POSITIONS FOR MULTIPLE SURGICAL MOUNTING PLATFORM ROTATION CLUTCH BUTTONS

CROSS REFERENCE TO RELATED APPLICATIONS

This application claims priority to U.S. Provisional Patent Application No. 61/954,298 filed Mar. 17, 2014, the entirety of which is incorporated by reference.

BACKGROUND

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive robotic surgical or telesurgical systems have been developed to increase a surgeon's dexterity and avoid some of the limitations on traditional minimally invasive techniques. (Teleoperated medical devices, such as surgical systems, are sometimes called robotic surgical systems because they incorporate robot technology). In telesurgery, the surgeon uses some form of remote control (e.g., a servomechanism or the like) to manipulate surgical instrument movements, rather than directly holding and moving the instruments by hand. In telesurgery systems, the surgeon can be provided with an image of the surgical site at a surgical workstation. While viewing a two or three dimensional image of the surgical site on a display, the surgeon performs the surgical procedures on the patient by manipulating master control devices, which in turn control motion of the servo-mechanically operated instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor that relays input commands from the master controllers to the associated robotic arm and instrument assemblies and back from the instrument and arm assemblies to the associated master controllers in the case of, for example, force feedback or the like. One example of a robotic surgical system is the DA VINCI® system commercialized by Intuitive Surgical, Inc. of Sunnyvale, Calif.

A variety of structural arrangements can be used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 7,594,912; 6,758,843; 6,246,200; and 5,800,423; the full disclosures of which are incorporated herein by reference. These linkages often make use of a parallelogram arrangement to hold an instrument having a shaft. Such a manipulator structure can constrain movement of the instrument so that the instrument pivots about a remote center of manipulation positioned in space along the length of the rigid shaft. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 7,763,015; 6,702,805; 6,676,669; 5,855,583; 5,808,665; 5,445,166; and 5,184,601; the full disclosures of which are incorporated herein by reference.

A variety of structural arrangements can also be used to support and position the robotic surgical manipulator and the surgical instrument at the surgical site during robotic surgery. Supporting linkage mechanisms (e.g., serial kinematic chains of two or more individual links, connected by movable joints, and the like), sometimes referred to as set-up joints, or set-up joint arms, are often used to position and align each manipulator with the respective incision point in a patient's body. A single linkage may include two or more individual component mechanical joints (or an infinite number, in the case of a continuously flexible structure), but as a whole be considered a single joint with two or more degrees of freedom corresponding to the individual component joints. The supporting linkage mechanism facilitates the alignment of a surgical manipulator with a desired surgical incision point and targeted anatomy. Exemplary supporting linkage mechanisms are described in U.S. Pat. Nos. 6,246,200; 6,788,018; 7,763,015; and 7,837,674 the full disclosures of which are incorporated herein by reference.

While the new telesurgical systems and devices have proven highly effective and advantageous, still further improvements are desirable. In general, improved minimally invasive robotic surgery systems are desirable. It would be particularly beneficial if these improved technologies enhanced the efficiency and ease of use of robotic surgical systems. For example, it would be particularly beneficial to increase maneuverability, improve space utilization in an operating room, provide a faster and easier set-up, inhibit collisions between robotic devices during use, and/or reduce the mechanical complexity and size of these new surgical systems.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The present invention generally provides improved robotic and/or surgical devices, systems, and methods. Kinematic linkage structures and associated control systems described herein are particularly beneficial in helping system users to arrange the robotic structure in preparation for use, including in preparation for a surgical procedure on a particular patient. Exemplary robotic surgical systems described herein may have one or more kinematic linkage sub-systems that are configured to help align a manipulator structure with the surgical work site. The joints of these set-up systems may be actively driven, passive (so that they are manually articulated and then locked into the desired configuration while the manipulator is used therapeutically), or a mix of both. Embodiments of the robotic systems described herein may employ a set-up mode in which one or more joints are initially held static by a brake or joint drive system. Inadvertent articulation is limited by the brake or drive system, but the user can manually actuate one of a plurality of inputs (e.g., depressible buttons) each positioned on one of the set-up joints supporting the plurality of manipulators to modify the signals transmitted to the brake or joint drive system to allow for manual movement of the one or more joints. When the user arrives at the desired configuration, the user may stop actuation of the input to reactuate the brake or drive system to limit inadvertent manual movement of the one or more joints thereafter. Embodiments of the invention provide a user interface that is intuitive, and can be particularly well-suited for manual movement of a platform supporting a plurality of surgical manipulators in a robotic surgical system or the like without having to add additional joint position or torque sensors or the like.

In some embodiments, a teleoperated surgical system is provided. The teleoperated surgical system may include a support structure supporting a mounting platform. The support structure may include a support linkage including a base and a drive or brake system operatively coupled to the support linkage so as to limit inadvertent manual rotation of the mounting platform relative to the support structure base. The teleoperated surgical system may further include a first manipulator and a second manipulator extending from and supported by the mounting platform. The first manipulator and the second manipulator may be coupled to the mounting platform via a first set-up linkage and a second set-up linkage, respectively. The teleoperated surgical system may further include a first actuatable input and a second actuatable input—each configured for user actuation of the drive or brake system to allow for manual rotation of the mounting platform by a user. The first actuatable input and the second actuatable input may be positioned on the first set-up linkage and second set-up linkage, respectively.

Optionally, the first and second actuatable inputs may each comprise switches. The switches may each comprise depressible buttons. In some embodiments, each of the first and second set-up linkages comprise a base link that extends horizontally from the mounting platform. The first and second actuatable inputs for user actuation of the drive or brake system may be positioned distally from the base link of each of the first and second set-up linkages, respectively. In some embodiments, the first and second set-up linkages may comprise a vertical link coupled with the base link that extends downwardly from an end of the base link. The first and second actuatable inputs may be positioned on or distally from the vertical link of each of the first and second set-up linkages, respectively.

In some embodiments a teleoperated surgical system may be provided that includes a support structure supporting a mounting platform. The support structure may include a support linkage including a base and a drive or brake system operatively coupled to the support linkage so as to limit inadvertent manual rotation of the mounting platform relative to the support structure base. The teleoperated surgical system may further include a plurality of manipulators extending from and supported by the mounting platform. The plurality of manipulators may each couple to the mounting platform via a set-up linkage. The teleoperated surgical system may further include a plurality of actuatable inputs. The plurality of inputs may be positioned between an associated one of the plurality of manipulators and the mounting platform. A processor may be provided that couples with the plurality of actuatable inputs and the drive or brake system. The processor may be configured to actuate the drive or brake system to allow for manual rotation of the mounting platform by a user when the user actuates any one of the plurality of actuatable inputs.

Optionally, the plurality of actuatable inputs may be switches. In some embodiments, the switches may be depressible buttons. In some embodiments, each of the set-up linkages may include a base link that extends horizontally from the mounting platform. The plurality of actuatable inputs for user actuation of the drive or brake system may be positioned distally from the base link of each of the set-up linkages, respectively. In some embodiments each of the set-up linkages may include a vertical link coupled with the base link that extends downwardly from an end of the base link. The plurality of actuatable inputs may be positioned on or distally from the vertical link of each of the set-up linkages, respectively.

In some embodiments, a method of positioning one or more manipulators of a teleoperated surgical system is provided. The method may include providing a teleoperated surgical system including a support structure supporting a mounting platform. The support structure may include a support linkage including a base and a drive or brake system operatively coupled to the support linkage. The teleoperated surgical system may further include a plurality of manipulators extending from and supported by the mounting platform. The plurality of manipulators may each couple to the mounting platform via a set-up linkage. The teleoperated surgical system may further include a plurality of actuatable inputs. The plurality of inputs may each be positioned between an associated one of the plurality of manipulators and the mounting platform. The method may further include actuating the drive or brake system so as to limit inadvertent manual rotation of the mounting platform relative to the support structure base. The method may further include receiving a signal from any one of the plurality of actuatable inputs indicating user actuation of one of the actuatable inputs. Thereafter, the method may include actuating the drive or brake system so as to allow for manual rotation of the mounting platform by a user so long as the signal is being received from any one of the plurality of actuatable inputs. The method may further include reactuating the drive or brake system so as to limit inadvertent manual rotation of the mounting platform once the signal from any one of the plurality of actuatable inputs is no longer received.

In some embodiments, the plurality of actuatable inputs comprise switches. Optionally, the switches comprise depressible buttons.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The kinematic linkage structures and control systems described herein are particularly beneficial in helping system users to arrange the robotic structure of a procedure on a particular patient. Along with actively driven manipulators used to interact with tissues and the like during treatment, robotic surgical systems may have one or more kinematic linkage systems that are configured to support and help align the manipulator structure with the surgical work site. These set-up systems may be actively driven or may be passive, so that they are manually articulated and then locked into the desired configuration while the manipulator is used therapeutically. The passive set-up kinematic systems may have advantages in size, weight, complexity, and cost. Unfortunately, a plurality of manipulators may be used to treat tissues of each patient, the manipulators may each independently benefit from accurate positioning so as to allow the instrument supported by that instrument to have the desired motion throughout the workspace, and minor changes in the relative locations of adjacent manipulators may have significant impact on the interactions between manipulators (with poorly positioned manipulators potentially colliding or having their range and/or ease of motion significantly reduced). Hence, the challenges of quickly arranging the robotic system in preparation for surgery can be significant.

One option is to mount multiple manipulators to a single platform, with the manipulator-supporting platform sometimes being referred to as an orienting platform. The orienting platform can be supported by an actively driven support linkage (sometimes referred to herein as a set-up structure, and typically having a set-up structure linkage, etc.) The system may also provide and control motorized axes of the robotic set-up structure supporting the orienting platform with some kind of joystick or set of buttons that would allow the user to actively drive those axes as desired in an independent fashion. This approach, while useful in some situations, may suffer from some disadvantages. In particular, it may be difficult to locate a drive button for all the elements of a complex system so that each is accessible to users approaching the system in all its potential configurations. Furthermore, both sterile and non-sterile members of a surgical team may want to articulate some joints or linkages (such as by grabbing differing locations inside or outside the sterile field). Hence a more intuitive and flexible user interface would be desirable. This is particularly true of an orienting platform for use in multi-quadrant surgery, or for a structure that supports a plurality of surgical manipulators and may pivot about an axis extending at least roughly vertically so as to orient the manipulators relative to a patient on a surgical table or other support.

Minimally Invasive Robotic Surgery

Figure 1:
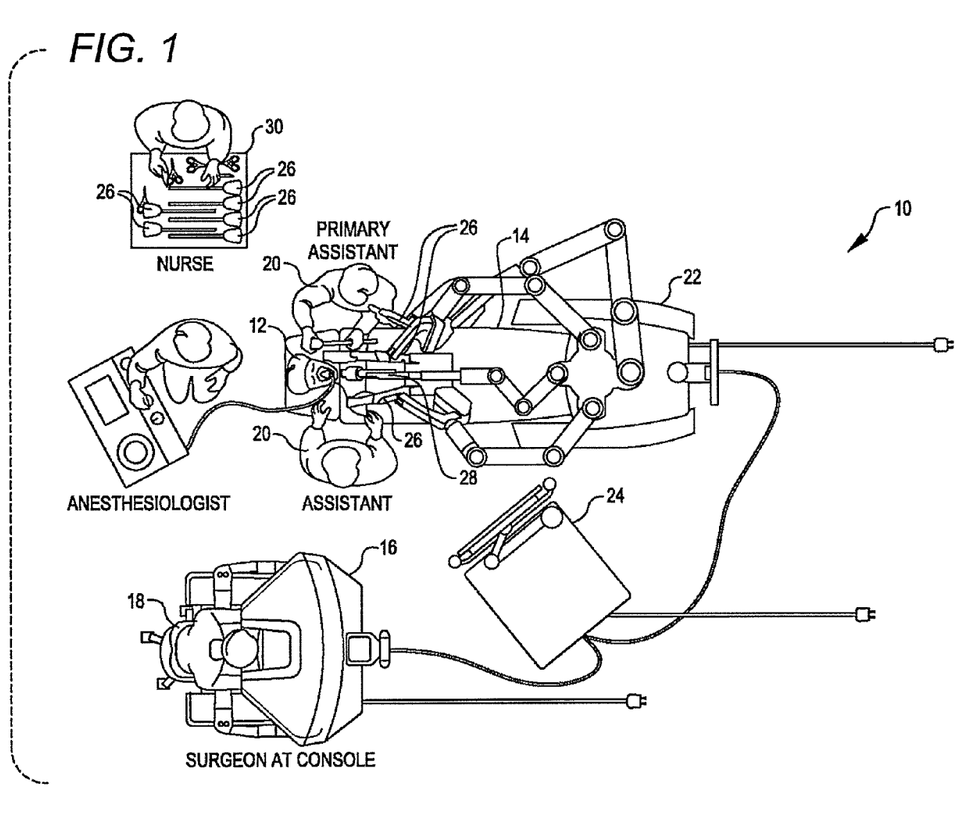
FIG. 1 is a plan view of a minimally invasive robotic surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
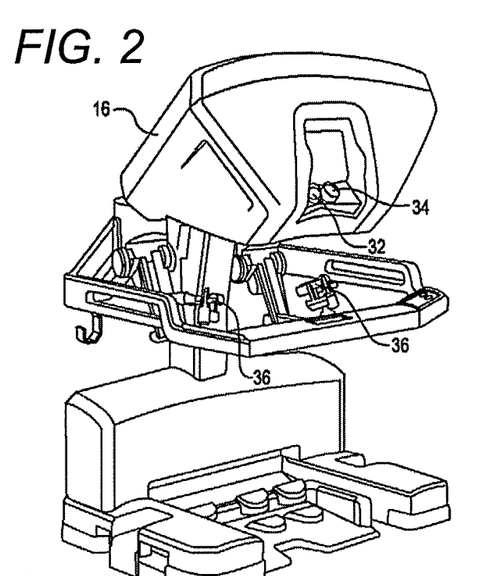
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
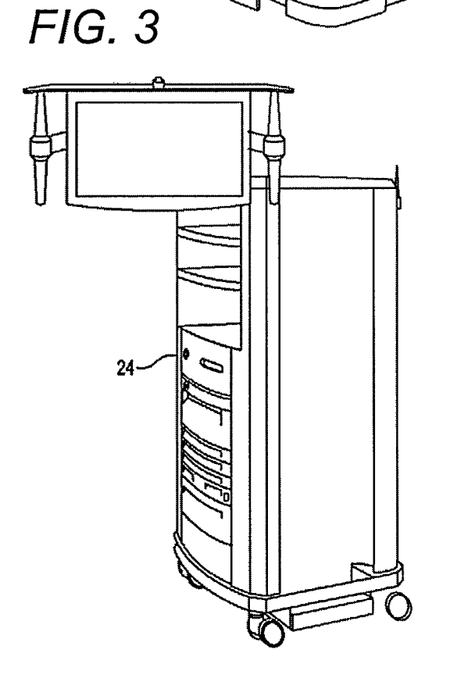
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
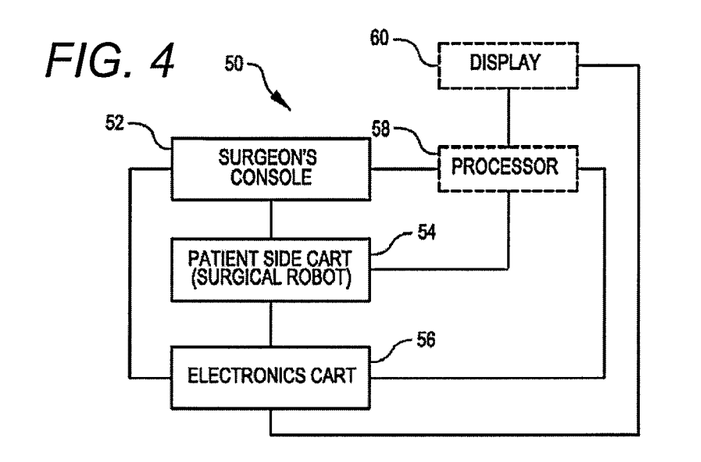
FIG. 4 diagrammatically illustrates a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Processor 58 will typically include a combination of hardware and software, with the software comprising tangible media embodying computer readable code instructions for performing the method steps of the control functionally described herein. The hardware typically includes one or more data processing boards, which may be co-located but will often have components distributed among the robotic structures described herein. The software will often comprise a non-volatile media, and could also comprise a monolithic code but will more typically comprise a number of subroutines, optionally running in any of a wide variety of distributed data processing architectures.

Figure 5A:
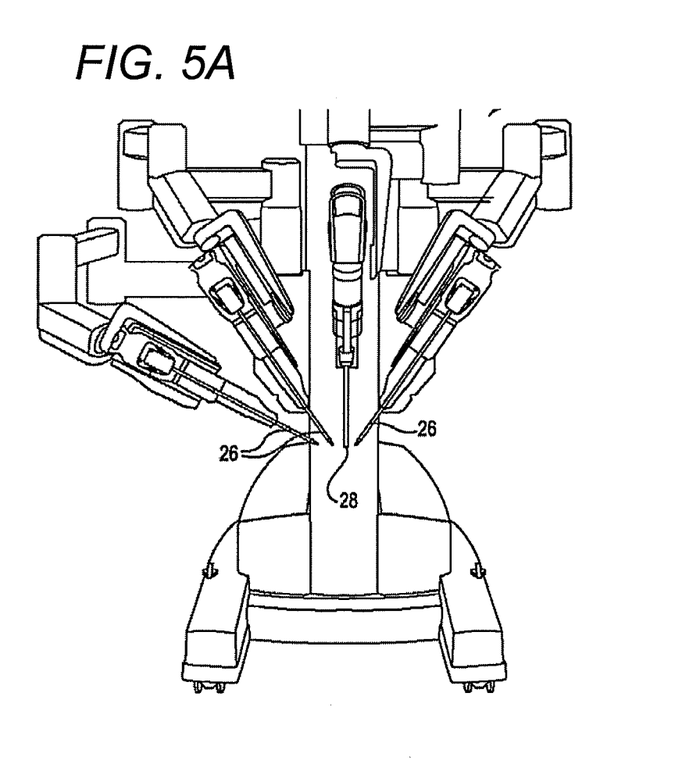
FIG. 5A is a partial view of a patient side cart (surgical robot) of a robotic surgery system, in accordance with many embodiments.
Figure 5B:
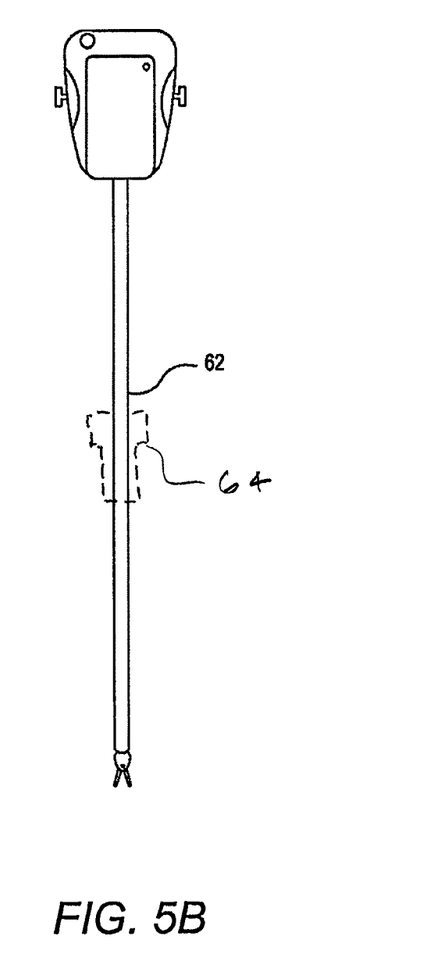
FIG. 5B is a front view of a robotic surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Surgical tools 26 are inserted into the patient by inserting a tubular cannula 64 through a minimally invasive access aperture such as an incision, natural orifice, percutaneous penetration, or the like. Cannula 64 is mounted to the robotic manipulator arm and the shaft of surgical tool 26 passes through the lumen of the cannula. The manipulator arm may transmit signals indicating that the cannula has been mounted thereon.

Robotic Surgery Systems and Modular Manipulator Supports

Figure 6:
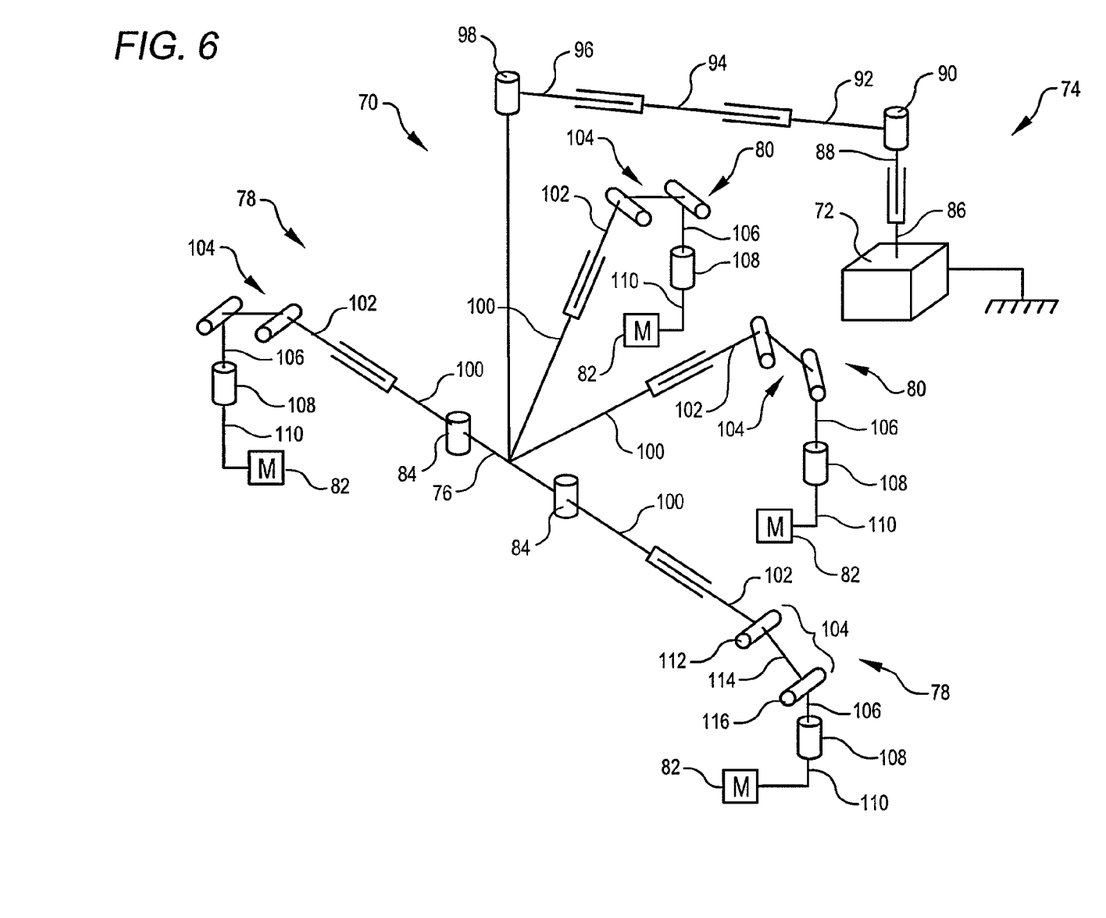
FIG. 6 is a perspective schematic representation of a robotic surgery system, in accordance with many embodiments.

FIG. 6 is a perspective schematic representation of a robotic surgery system 70, in accordance with many embodiments. The surgery system 70 includes a mounting base 72, a support linkage 74, an orienting platform 76, a plurality of outer set-up linkages 78 (two shown), a plurality of inner set-up linkages 80 (two shown), and a plurality of surgical instrument manipulators 82. Each of the manipulators 82 is operable to selectively articulate a surgical instrument mounted to the manipulator 82 and insertable into a patient along an insertion axis. Each of the manipulators 82 is attached to and supported by one of the set-up linkages 78, 80. Each of the outer set-up linkages 78 is rotationally coupled to and supported by the orienting platform 76 by a first set-up linkage joint 84. Each of the inner set-up linkages 80 is fixedly attached to and supported by the orienting platform 76. The orienting platform 76 is rotationally coupled to and supported by the support linkage 74. And the support linkage 74 is fixedly attached to and supported by the mounting base 72.

In many embodiments, the mounting base 72 is a movable and floor supported, thereby enabling selective repositioning of the overall surgery system 70, for example, within an operating room. The mounting base 72 can include a steerable wheel assembly and/or any other suitable support features that provide for both selective repositioning as well as selectively preventing movement of the mounting base 72 from a selected position. The mounting base 72 can also have other suitable configurations, for example, a ceiling mount, fixed floor/pedestal mount, a wall mount, or an interface configured for being supported by any other suitable mounting surface.

The support linkage 74 is operable to selectively position and/or orient the orienting platform 76 relative to the mounting base 72. The support linkage 74 includes a column base 86, a translatable column member 88, a shoulder joint 90, a boom base member 92, a boom first stage member 94, a boom second stage member 96, and a wrist joint 98. The column base 86 is fixedly attached to the mounting base 72. The translatable column member 88 is slideably coupled to the column base 86 for translation relative to column base 86. In many embodiments, the translatable column member 88 translates relative to the column base 86 along a vertically oriented axis. The boom base member 92 is rotationally coupled to the translatable column member 88 by the shoulder joint 90. The shoulder joint 90 is operable to selectively orient the boom base member 92 in a horizontal plane relative to the translatable column member 88, which has a fixed angular orientation relative to the column base 86 and the mounting base 72. The boom first stage member 94 is selectively translatable relative to the boom base member 92 in a horizontal direction, which in many embodiments is aligned with both the boom base member 92 and the boom first stage member 94. The boom second stage member 96 is likewise selectively translatable relative to the boom first stage member 94 in a horizontal direction, which in many embodiments is aligned with the boom first stage member 94 and the boom second stage member 96. Accordingly, the support linkage 74 is operable to selectively set the distance between the shoulder joint 90 and the distal end of the boom second stage member 96. The wrist joint 98 rotationally couples the distal end of the boom second stage member 96 to the orienting platform 76. The wrist joint 98 is operable to selectively set the angular orientation of the orienting platform 76 relative to the mounting base 72.

Each of the set-up linkages 78, 80 is operable to selectively position and/or orient the associated manipulator 82 relative to the orienting platform 76. Each of the set-up linkages 78, 80 includes a set-up linkage base link 100, a set-up linkage extension link 102, a set-up linkage parallelogram linkage portion 104, a set-up linkage vertical link 106, a second set-up linkage joint 108, and a manipulator support link 110. In each of the set-up linkage base links 100 of the outer set-up linkages 78 can be selectively oriented relative to the orienting platform 76 via the operation of the a first set-up linkage joint 84. In the embodiment shown, each of the set-up linkage base links 100 of the inner set-up linkages 80 is fixedly attached to the orienting platform 76. Each of the inner set-up linkages 80 can also be rotationally attached to the orienting platform 76 similar to the outer set-up linkages via an additional first set-up linkage joints 84. Each of the set-up linkage extension links 102 is translatable relative to the associated set-up linkage base link 100 in a horizontal direction, which in many embodiments is aligned with the associated set-up linkage base link and the set-up linkage extension link 102. Each of the set-up linkage parallelogram linkage portions 104 configured and operable to selectively translate the set-up linkage vertical link 106 in a vertical direction while keeping the set-up linkage vertical link 106 vertically oriented. In example embodiments, each of the set-up linkage parallelogram linkage portions 104 includes a first parallelogram joint 112, a coupling link 114, and a second parallelogram 116. The first parallelogram joint 112 rotationally couples the coupling link 114 to the set-up linkage extension link 102. The second parallelogram joint 116 rotationally couples the set-up linkage vertical link 106 to the coupling link 114. The first parallelogram joint 112 is rotationally tied to the second parallelogram joint 116 such that rotation of the coupling link 114 relative to the set-up linkage extension link 102 is matched by a counteracting rotation of the set-up linkage vertical link 106 relative to the coupling link 114 so as to maintain the set-up linkage vertical link 106 vertically oriented while the set-up linkage vertical link 106 is selectively translated vertically. The second set-up linkage joint 108 is operable to selectively orient the manipulator support link 110 relative to the set-up linkage vertical link 106, thereby selectively orienting the associated attached manipulator 82 relative to the set-up linkage vertical link 106.

Figure 7:
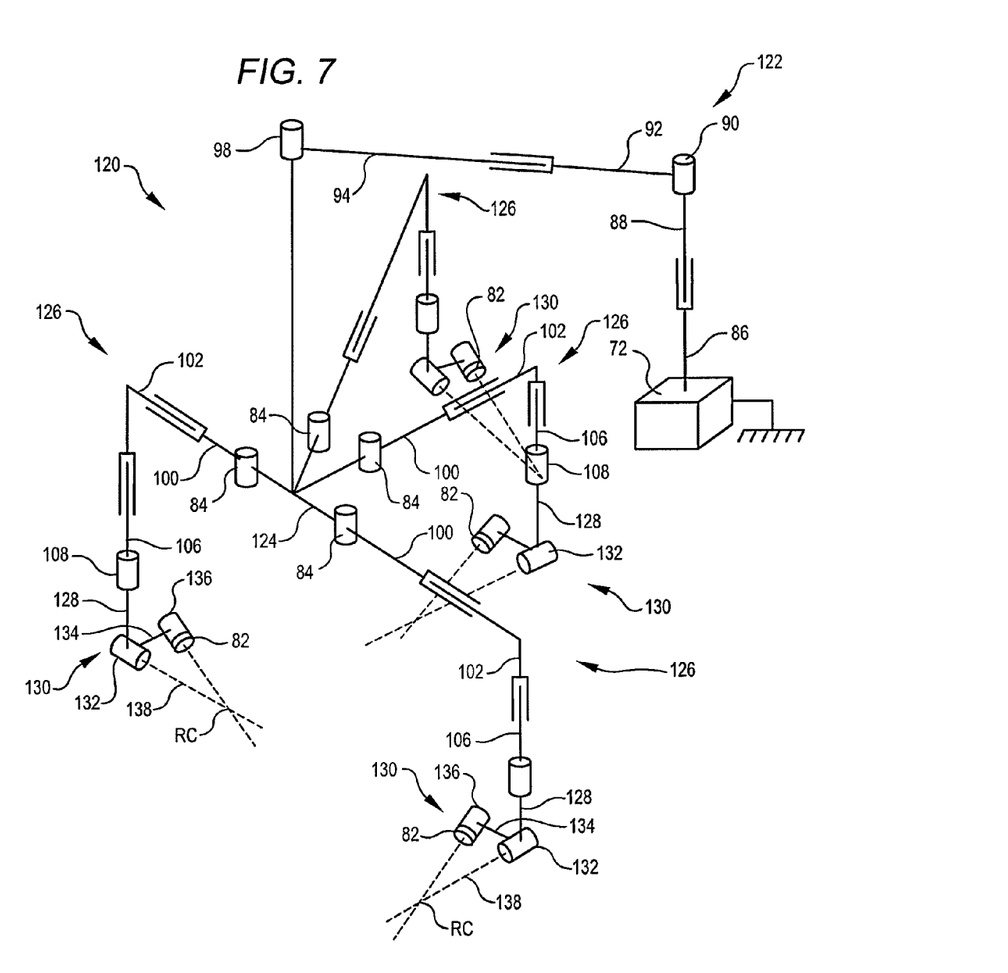
FIG. 7 is a perspective schematic representation of another robotic surgery system, in accordance with many embodiments.

FIG. 7 is a perspective schematic representation of a robotic surgery system 120, in accordance with many embodiments. Because the surgery system 120 includes components similar to components of the surgery system 70 of FIG. 6, the same reference numbers are used for similar components and the corresponding description of the similar components set forth above is applicable to the surgery system 120 and is omitted here to avoid repetition. The surgery system 120 includes the mounting base 72, a support linkage 122, an orienting platform 124, a plurality of set-up linkages 126 (four shown), and a plurality of the surgical instrument manipulators 82. Each of the manipulators 82 is operable to selectively articulate a surgical instrument mounted to the manipulator 82 and insertable into a patient along an insertion axis. Each of the manipulators 82 is attached to and supported by one of the set-up linkages 126. Each of the set-up linkages 126 is rotationally coupled to and supported by the orienting platform 124 by the first set-up linkage joint 84. The orienting platform 124 is rotationally coupled to and supported by the support linkage 122. And the support linkage 122 is fixedly attached to and supported by the mounting base 72.

The support linkage 122 is operable to selectively position and/or orient the orienting platform 124 relative to the mounting base 72. The support linkage 122 includes the column base 86, the translatable column member 88, the shoulder joint 90, the boom base member 92, the boom first stage member 94, and the wrist joint 98. The support linkage 122 is operable to selectively set the distance between the shoulder joint 90 and the distal end of the boom first stage member 94. The wrist joint 98 rotationally couples the distal end of the boom first stage member 94 to the orienting platform 124. The wrist joint 98 is operable to selectively set the angular orientation of the orienting platform 124 relative to the mounting base 72.

Each of the set-up linkages 126 is operable to selectively position and/or orient the associated manipulator 82 relative to the orienting platform 124. Each of the set-up linkages 126 includes the set-up linkage base link 100, the set-up linkage extension link 102, the set-up linkage vertical link 106, the second set-up linkage joint 108, a tornado mechanism support link 128, and a tornado mechanism 130. Each of the set-up linkage base links 100 of the set-up linkages 126 can be selectively oriented relative to the orienting platform 124 via the operation of the associated first set-up linkage joint 84. Each of the set-up linkage vertical links 106 is selectively translatable in a vertical direction relative to the associated set-up linkage extension link 102. The second set-up linkage joint 108 is operable to selectively orient the tornado mechanism support link 128 relative to the set-up linkage vertical link 106

Each of the tornado mechanisms 130 includes a tornado joint 132, a coupling link 134, and a manipulator support 136. The coupling link 134 fixedly couples the manipulator support 136 to the tornado joint 132. The tornado joint 130 is operable to rotate the manipulator support 136 relative to the tornado mechanism support link 128 around a tornado axis 136. The tornado mechanism 128 is configured to position and orient the manipulator support 134 such that the remote center of manipulation (RC) of the manipulator 82 is intersected by the tornado axis 136. Accordingly, operation of the tornado joint 132 can be used to reorient the associated manipulator 82 relative to the patient without moving the associated remote center of manipulation (RC) relative to the patient.

Figure 8:
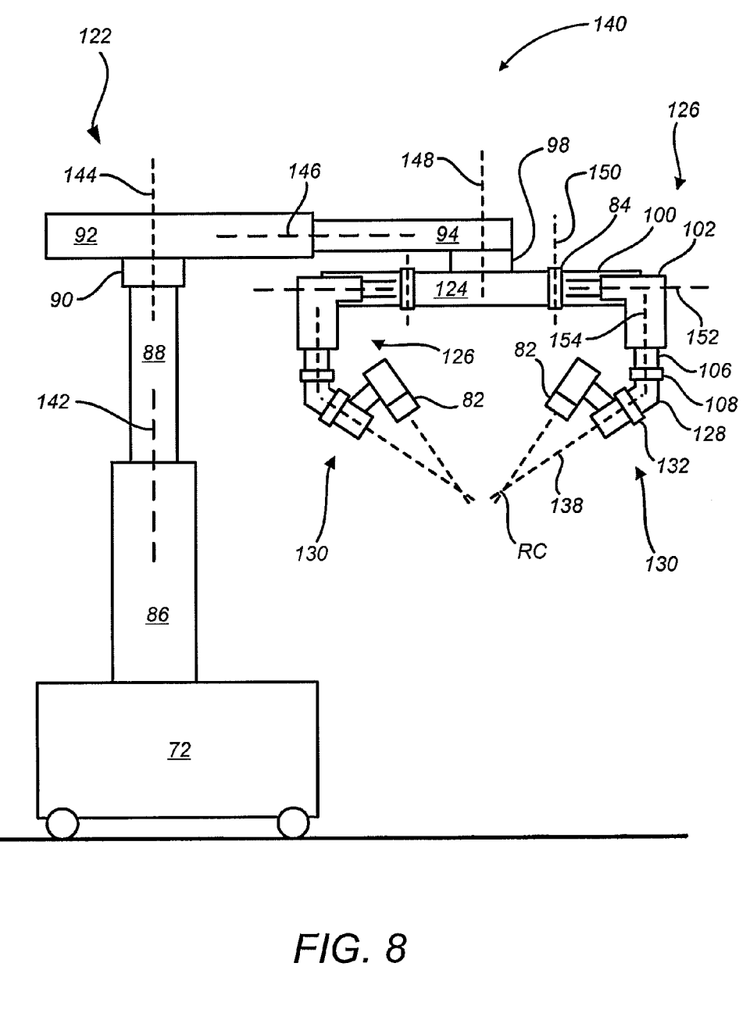
FIG. 8 shows a robotic surgery system, in accordance with many embodiments, in conformance with the schematic representation of FIG. 7.

FIG. 8 is a simplified representation of a robotic surgery system 140, in accordance with many embodiments, in conformance with the schematic representation of the robotic surgery system 120 of FIG. 7. Because the surgery system 140 conforms to the robotic surgery system 120 of FIG. 7, the same reference numbers are used for analogous components and the corresponding description of the analogous components set forth above is applicable to the surgery system 140 and is omitted here to avoid repetition.

The support linkage 122 is configured to selectively position and orient the orienting platform 124 relative to the mounting base 72 via relative movement between links of the support linkage 122 along multiple set-up structure axes. The translatable column member 88 is selectively repositionable relative to the column base 86 along a first set-up structure (SUS) axis 142, which is vertically oriented in many embodiments. The shoulder joint 90 is operable to selectively orient the boom base member 92 relative to the translatable column member 88 around a second SUS axis 144, which is vertically oriented in many embodiments. The boom first stage member 94 is selectively repositionable relative to the boom base member 92 along a third SUS axis 146, which is horizontally oriented in many embodiments. The wrist joint 98 is operable to selectively orient the orienting platform 124 relative to the boom first stage member 94 around a fourth SUS axis 148, which is vertically oriented in many embodiments.

Each of the set-up linkages 126 is configured to selectively position and orient the associated manipulator 82 relative to the orienting platform 124 via relative movement between links of the set-up linkage 126 along multiple set-up joint (SUJ) axes. Each of the first set-up linkage joint 84 is operable to selectively orient the associated set-up linkage base link 100 relative to the orienting platform 124 around a first SUJ axis 150, which in many embodiments is vertically oriented. Each of the set-up linkage extension links 102 can be selectively repositioned relative to the associated set-up linkage base link 10 along a second SUJ axis 152, which is horizontally oriented in many embodiments. Each of the set-up linkage vertical links 106 can be selectively repositioned relative to the associated set-up linkage extension link 102 along a third SUJ axis 154, which is vertically oriented in many embodiments. Each of the second set-up linkage joints 108 is operable to selectively orient the tornado mechanism support link 128 relative to the set-up linkage vertical link 106 around the third SUJ axis 154. Each of the tornado joints 132 is operable to rotate the associated manipulator 82 around the associated tornado axis 138.

Figure 9:
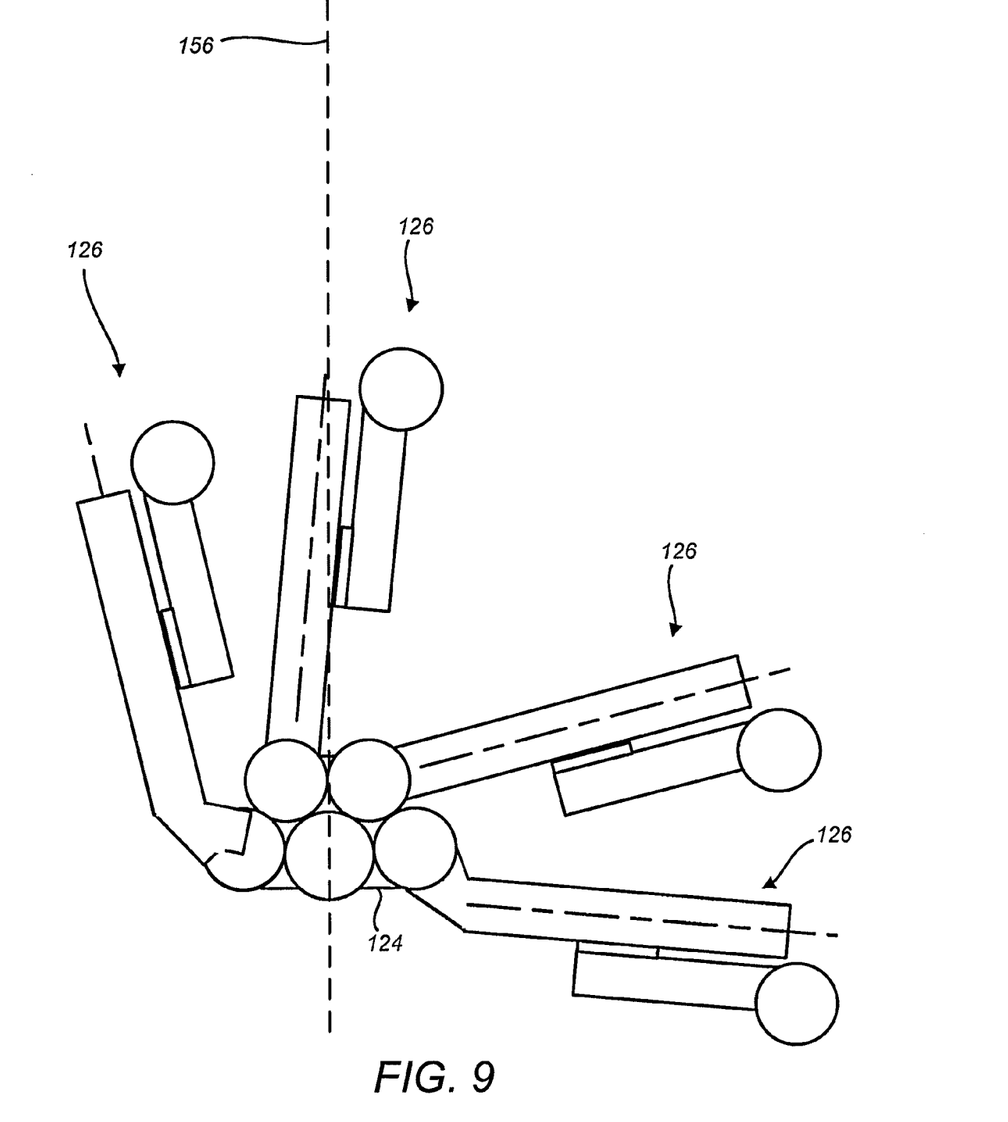
FIG. 9 illustrates rotational orientation limits of set-up linkages relative to an orienting platform of the robotic surgery system of FIG. 8.

FIG. 9 illustrates rotational orientation limits of the set-up linkages 126 relative to the orienting platform 124, in accordance with many embodiments. Each of the set-up linkages 126 is shown in a clockwise limit orientation relative to the orienting platform 124. A corresponding counter-clockwise limit orientation is represented by a mirror image of FIG. 9 relative to a vertically-oriented mirror plane. As illustrated, each of the two inner set-up linkages 126 can be oriented from 5 degrees from a vertical reference 156 in one direction to 75 degrees from the vertical reference 156 in the opposite direction. And as illustrated, each of the two outer set-up linkages can be oriented from 15 degrees to 95 degrees from the vertical reference 156 in a corresponding direction.

In use, it will often be desirable for a surgical assistant, surgeon, technical support, or other user to configure some or all of the linkages of robotic surgical system 140 (FIG. 8) for surgery, including the set-up structure linkage, the set-up joints, and/or each of the manipulators. Included among the task in configuring these linkages will be positioning the orienting platform 124 relative to first stage member 94 about vertical fourth SUS axis 148 of wrist joint 98. A joint drive motor and/or brake system is coupled to wrist joint 98, with one exemplary embodiment including both a drive and brake. Additionally, a joint sensor system will typically sense an angular configuration or position of wrist joint 98.

An exemplary user interface, system, and method for manually configuring the system for use will be described herein with reference to manual articulation of orienting platform 124 by articulation of wrist joint 98 about fourth SUS axis 148. It should be understood that alternative embodiments may be employed to articulate one or more alternative joints of the overall kinematic system, including one or more alternative joints of the set-up structure, one or more of the set-up joints, or one or more of the joints of the manipulators linkages. Use of the exemplary embodiment for articulating the motorized wrist joint embodiments may allow a user to efficiently position manipulators 82. The manual articulation of wrist joint 98 as described herein can improve speed and ease of use while manually docking manipulators 82 to their associated cannulas 64, as shown in FIG. 5B.

Figure 10:
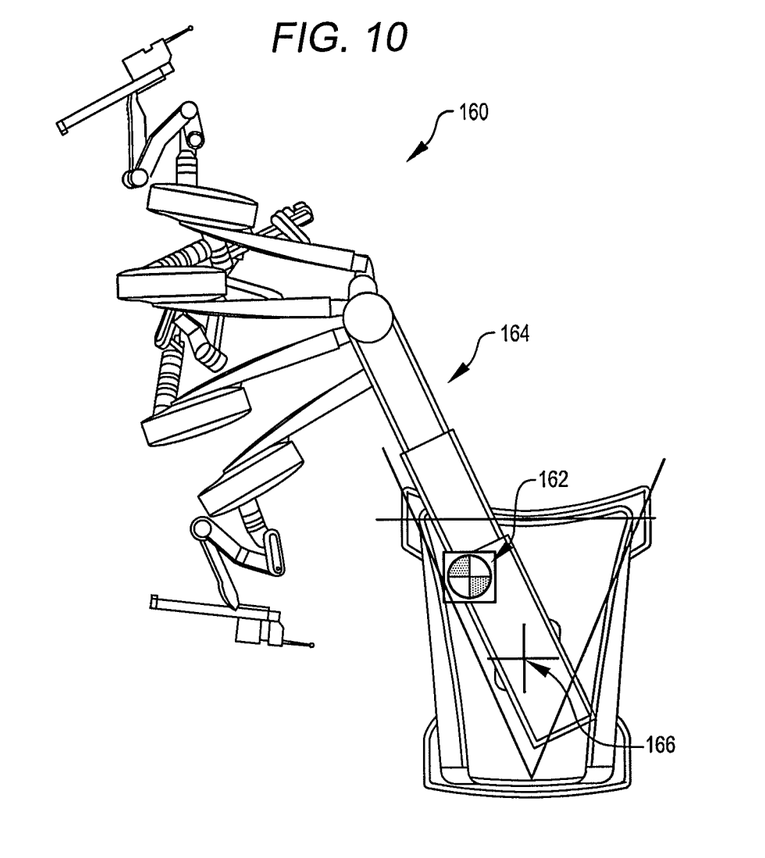
FIG. 10 shows a center of gravity diagram associated with a rotational limit of the boom assembly for a robotic surgery system, in accordance with many embodiments.

FIG. 10 shows a center of gravity diagram associated with a rotational limit of a support linkage for a robotic surgery system 160, in accordance with many embodiments. With components of the robotic surgery system 160 positioned and oriented to shift the center-of-gravity 162 of the robotic surgery system 160 to a maximum extent to one side relative to a support linkage 164 of the surgery system 160, a shoulder joint of the support linkage 164 can be configured to limit rotation of the support structure 164 around a set-up structure (SUS) shoulder-joint axis 166 to prevent exceeding a predetermined stability limit of the mounting base.

Figure 11:
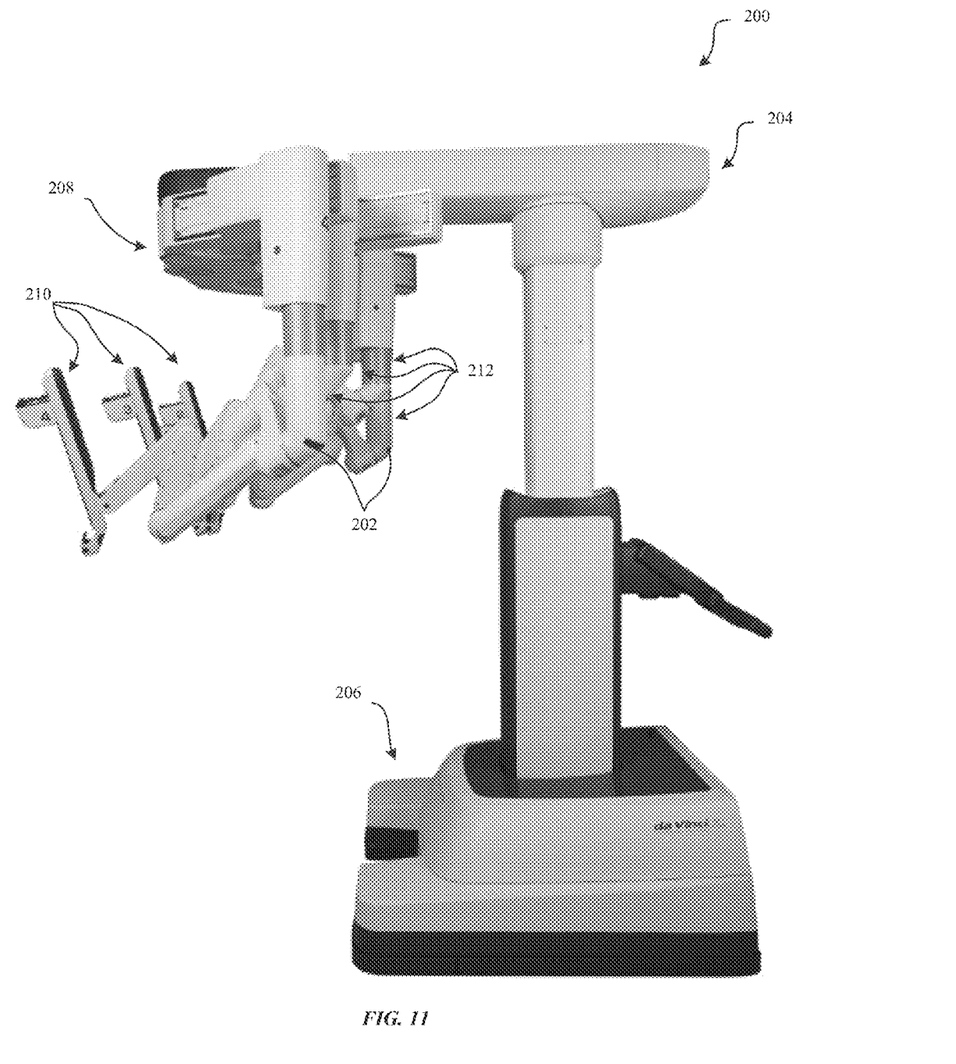
FIG. 11 shows an exemplary system and the positioning of mounting platform rotation buttons according to some embodiments of the invention.

The robotic system may include a configuration mode which allows a user to manually configure the orienting platform in a desired orientation about fourth SUS axis 148. In some embodiments, the robotic system may enter the configuration mode when the user actuates one of a plurality of inputs positioned on associated set-up joint linkages. For example, FIG. 11 shows an exemplary teleoperated surgical system 200 which includes a plurality of inputs 202 for entering the configuration mode. The teleoperated surgical system 200 includes a set-up structure 204. The set-up structure 204 includes a base 205, a column 206, and a horizontal boom 207, and supports an mounting/orienting platform 208. A plurality of manipulators 210 are supported from the mounting platform 208 via set-up joint linkages 212. The set-up joint linkages 212 extend from and are supported by the orienting platform 208. The plurality of inputs 202 may be positioned on each of the set-up joint linkages 212 so that a user may enter the configuration mode by actuating any one of the plurality inputs 202 on each of the set-up joint linkages 212. In some embodiments, the inputs 202 may be switches. In some embodiments, the switches may be depressible buttons, or the like. In some embodiments, a safety measure may be provided where, when a cannula is mounted to any of the manipulators supported by platform 124, the system may apply the brake to the wrist joint 98 and exit the configuration mode or prevent entry into the configuration mode so as to inhibit manual movement of the wrist joint.

While the system is not in the configuration mode, the system processor will typically transmit signals to the joint motor or brake associated with wrist joint 98 so as to keep the platform in its initial position so as to reduce inadvertent manual rotation of the platform. Hence, when the system is bumped, pushed, or pulled lightly the wrist motor may prevent movement or urge the platform back toward the initial position by applying a joint torque per an error E that varies with the difference between the sensed joint position (θ) and the initial joint position (θ$_I$):

$$E=\theta-\theta_I$$

The servo control may also be achieved by using a torque that is proportional to the difference between sensed position and initial position. This driving of the joint toward the initial pose may be overcome by user actuation of any one of the plurality of inputs 202 that enter the system 200 into the configuration mode. For example, the system may enter the configuration mode when the user presses and holds one of the inputs 202. When in the configuration mode, the processor may halt servoing of the wrist joint to counteract articulation of the joint so as to allow a user to manually rotate the platform from its initial position toward a desired position. In some embodiments, it may be advantageous to provide an input on each of the set-up joint linkages between the manipulator and the platform so as to provide a number inputs that are convenient for user actuation. Further, positioning a plurality of inputs on the set-up joint linkages may provide an effective moment arm for rotating the orienting platform to a desired position.

Although servoing so as to counteract the user movement of the platform is halted when the system is in a configuration mode, drive signals may still be sent to the wrist motor. For example, friction compensation, gravity compensation, momentum compensation, and/or the like may be provided by applying appropriate drive signals during manual movement of the platform. Exemplary compensation drive systems are more fully described in US Patent Publication 2009/0326557 in the name of Neimeyer and entitled "Friction Compensation in a Minimally Invasive Surgical Apparatus," in US Patent Publication 2011/0009880 in the name of Prisco et al. and entitled "Control System for Reducing Internally Generated Frictional and Inertial Resistance to Manual Positioning of a Surgical Manipulator," and the like. In some embodiments, the system may employ joint range of motion limits alone or in addition to the drive signals when servoing is halted. Such range of motion limits may respond similar to servoing when a user pushes beyond a range motion limit except they are one sided.

Once the user has manually articulated the wrist at the desired orientation, the user may halt movement of the platform and release the input 202 to exit the configuration mode. When the system exits the configuration mode, signals may then be resent to the brake or drive system to maintain the orienting platform in the desired orientation and to reduce inadvertent manual rotation of the orienting platform.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A teleoperated surgical system comprising:
   a support structure supporting a mounting platform, the support structure including a support linkage including a base and a drive or brake system operatively coupled to the support linkage so as to limit inadvertent manual rotation of the mounting platform relative to the support structure base;
   a first manipulator and a second manipulator extending from and supported by the mounting platform, the first manipulator and the second manipulator coupled to the mounting platform via a first set-up linkage and a second set-up linkage, respectively;
   a first actuatable input and a second actuatable input, each configured for user actuation of the drive or brake system of the support structure to selectively halt a servoing or a braking by the drive or brake system that limits the inadvertent manual rotation of the mounting platform relative to the support structure base to allow for manual rotation of the mounting platform by a user, the first actuatable input and second actuatable input positioned on the first set-up linkage and second set-up linkage, respectively.

2. The teleoperated surgical system of claim 1, wherein the first and second actuatable inputs each comprise switches.

3. The teleoperated surgical system of claim 2, wherein the first and second switches each comprise depressible buttons.

4. The teleoperated surgical system of claim 1, wherein each of the first and second set-up linkages comprise a base link that extends horizontally from the mounting platform and wherein the first and second actuatable inputs for user actuation of the drive or brake system are positioned distally from the base link of each of the first and second set-up linkages, respectively.

5. The teleoperated surgical system of claim 4, wherein each of the first and second set-up linkages comprise a vertical link coupled with the base link that extends down from an end of the base link, and wherein the first and second actuatable inputs are positioned on the vertical link of each of the first and second set-up linkages, respectively.

6. A teleoperated surgical system comprising:
a support structure supporting a mounting platform, the support structure including a support linkage including a base and a drive or brake system operatively coupled to the support linkage so as to limit inadvertent manual rotation of the mounting platform relative to the support structure base;
a plurality of manipulators extending from and supported by the mounting platform, the plurality of manipulators each coupled to the mounting platform via a set-up linkage;
a plurality of actuatable inputs, the plurality of inputs each positioned between an associated one of the plurality of manipulators and the mounting platform; and
a processor coupling with the plurality of actuatable inputs and the drive or brake system, the processor configured to actuate the drive or brake system to selectively halt a servoing or a braking by the drive or brake system that limits the inadvertent manual rotation of the mounting platform relative to the support structure base based on input from the actuatable inputs so as to allow for manual rotation of the mounting platform by a user when the user actuates any one of the plurality of actuatable inputs.

7. The teleoperated surgical system of claim 6, wherein the plurality of actuatable inputs comprise switches.

8. The teleoperated surgical system of claim 7, wherein the switches comprise depressible buttons.

9. The teleoperated surgical system of claim 6, wherein each of the set-up linkages comprise a base link that extends horizontally from the mounting platform and wherein the plurality of actuatable inputs for user actuation of the drive or brake system are positioned distally from the base link of each of the set-up linkages, respectively.

10. The teleoperated surgical system of claim 9, wherein each of the set-up linkages comprise a vertical link coupled with the base link that extends down from an end of the base link, and wherein the plurality of actuatable inputs are positioned on the vertical link of each of the set-up linkages, respectively.

11. A method of positioning one or more manipulators of a teleoperated surgical system, the method comprising:
providing a teleoperated surgical system comprising:
a support structure supporting a mounting platform, the support structure including a support linkage including a base and a drive or brake system operatively coupled to the support linkage;
a plurality of manipulators extending from and supported by the mounting platform, the plurality of manipulators each coupled to the mounting platform via a set-up linkage;
a plurality of actuatable inputs, the plurality of inputs each positioned between an associated one of the plurality of manipulators and the mounting platform;
actuating the drive or brake system so as to limit inadvertent manual rotation of the mounting platform relative to the support structure base;
receiving a signal from any one of the plurality of actuatable inputs indicating user actuation of one of the actuatable inputs;
actuating the drive or brake system so as to halt a servoing or a braking by the drive or brake system that limits the inadvertent manual rotation of the mounting platform relative to the support structure base to allow for manual rotation of the mounting platform by a user so long as the signal is being received from any one of the plurality of actuatable inputs;
reactuating the drive or brake system so as to limit inadvertent manual rotation of the mounting platform once the signal from any one of the plurality of actuatable inputs is no longer received.

12. The method of claim 11, wherein the plurality of actuatable inputs comprise switches.

13. The method of claim 12, wherein the switches comprise depressible buttons.

14. The method of claim 11, wherein each of the set-up linkages comprise a base link that extends horizontally from the mounting platform and wherein the plurality of actuatable inputs for user actuation of the drive or brake system are positioned distally from the base link of each of the set-up linkages, respectively.

15. The method of claim 14, wherein each of the set-up linkages comprise a vertical link coupled with the base link that extends down from an end of the base link, and wherein the plurality of actuatable inputs are positioned on the vertical link of each of the set-up linkages, respectively.

* * * * *